(12) United States Patent
Masini

(10) Patent No.: US 6,187,012 B1
(45) Date of Patent: Feb. 13, 2001

(54) PROSTHETIC ELEMENT REMOVAL APPARATUS AND METHODS

(75) Inventor: Michael A. Masini, Ann Arbor, MI (US)

(73) Assignee: MedIdea, LLC, Ann Arbor, MI (US)

( * ) Notice: Under 35 U.S.C. 154(b), the term of this patent shall be extended for 0 days.

(21) Appl. No.: 09/349,281

(22) Filed: Jul. 8, 1999

(51) Int. Cl.⁷ .................................................. A61B 17/58
(52) U.S. Cl. ............................................................ 606/99
(58) Field of Search ................................ 623/22, 16, 18, 623/19; 606/72, 99, 100, 79, 84

(56) References Cited

U.S. PATENT DOCUMENTS

| | | | |
|---|---|---|---|
| 4,702,236 | * 10/1987 | Tarabichy et al. | 606/99 |
| 4,846,161 | * 7/1989 | Roger | 606/99 |
| 5,019,083 | * 5/1991 | Klapper et al. | 606/99 |
| 5,290,291 | * 3/1994 | Linden | 606/99 |
| 5,456,686 | * 10/1995 | Klapper et al. | 606/99 |
| 5,571,109 | * 11/1996 | Bertagnoli | 606/61 |

* cited by examiner

*Primary Examiner*—Michael Buiz
*Assistant Examiner*—(Jackie) Tan-Uyen Thi Ho
(74) *Attorney, Agent, or Firm*—Gifford, Krass, Groh, Sprinkle, Anderson & Citkowski, PC

(57) ABSTRACT

Guide means direct a cutting tool into the interface between a prosthesis and surrounding bone are provided to bring about a more controlled separation and removal thereof for revision or other purposes. Such guides may be placed on the prosthetic element itself or, alternatively, on a separate component aligned with the prosthesis. In the particular case of a stemmed prosthesis such as a proximal femoral component, the invention preferably provides one or more tracks, channels, grooves or slots longitudinally oriented along the stem of the implant, enabling an osteotome, for example, to be inserted thereinto and tapped down along the side of the implant between the prosthesis and the surrounding bone to bring about a cleaner and more controlled separation. Preferably, sufficient guide means are provided around the body of the implant so that as the cutting tool is inserted along the plurality of tracks, very little fusion remains between the implant and the surrounding bone, thereby enabling the prosthesis to be readily removed. Although different cutting tools may be provided for use as part of the invention, standard osteotomes are preferably used due to their widespread availability.

22 Claims, 4 Drawing Sheets

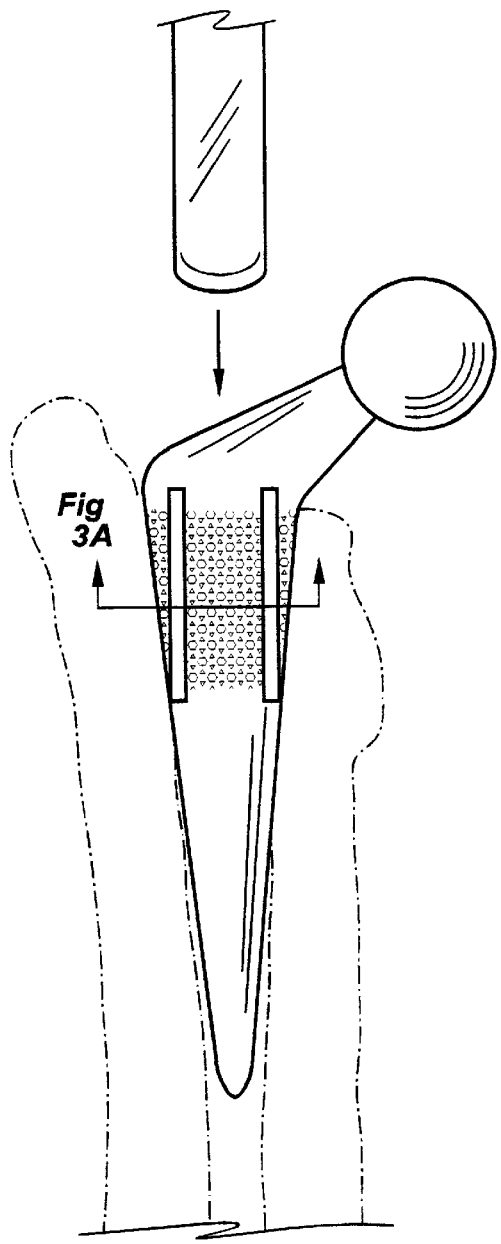 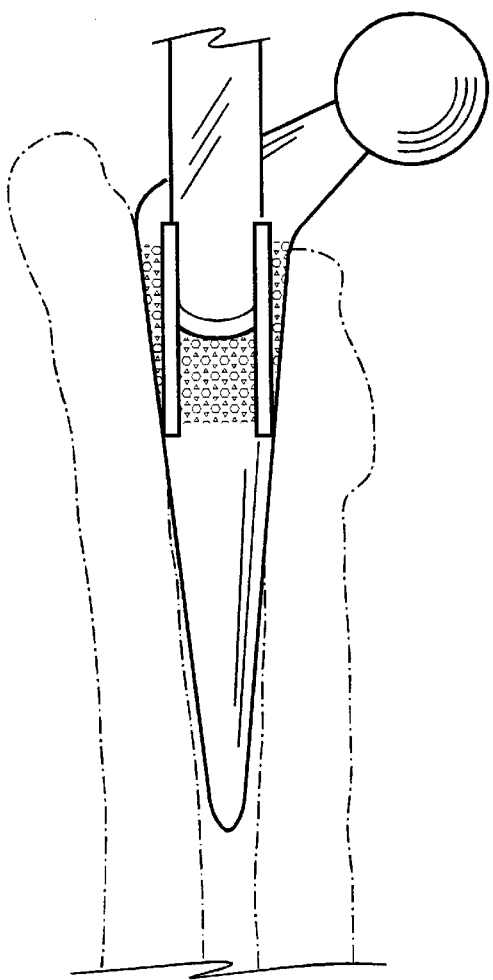
Fig - 2A    Fig - 2B

PROSTHETIC ELEMENT REMOVAL APPARATUS AND METHODS

FIELD OF THE INVENTION

This invention relates generally to prosthetic elements and, more particularly, to apparatus and methods for removing previously implanted orthopaedic appliances, including those associated with joint-replacement surgery.

BACKGROUND OF THE INVENTION

Porous or bony ingrowth surfaces are now commonly used on a wide variety of prosthetic elements, including joint-replacement components associated with the hip and knee, as well as other orthopaedic devices.

Although there is some debate as to the advantages of cementless fixation in terms of longevity and conservation of host bone, such devices are often very difficult to remove due to the tenacious invasion of surrounding bone. Removal for various purposes such as revision arthroplasty can therefore be unpredictable and problematic.

The need therefore exists for tools and techniques to aid in the removal of such devices. Such tools and techniques would preferably be applicable to both cemented as well as cementless fixation styles.

SUMMARY OF THE INVENTION

The present invention helps to minimize problems associated with the removal of prosthetic elements, both cemented and cementless, by providing guide means to direct a cutting tool into the interface between the prosthesis and the bone to effectuate a more controlled separation. In a preferred embodiment, such guide means are placed on the prosthetic element itself whereas, according to an alternative embodiment, the guide means are provided on a separate component which is then aligned with the prosthesis.

In the particular case of a stemmed prosthesis such as a proximal femoral component, the invention preferably provides one or more tracks, grooves, channels, slots or the like disposed longitudinally along the stem of the implant. Such guide means allows cutting tool such as an osteotome, for example, to be inserted thereinto and tapped down along the side of the implant between the prosthesis and the surrounding bone to bring about a cleaner and more controlled separation. Preferably, sufficient guide means are provided around the body of the implant so that as the cutting tool is inserted along the plurality of tracks, very little fusion remains between the implant and the surrounding bone, thereby enabling the prosthesis to be readily removed.

Although different cutting tools may be provided for use as part of the invention, standard osteotomes are preferably used due to their widespread availability. In particular, osteotomes having blades which are somewhat flexible are preferred in some applications, particularly when the stem to be released from the surrounding bone has a curved outer surface. As an alternative, however, specialized osteotomes or other cutting tools may be provided as discussed elsewhere herein to avoid binding or to cooperate with the guide means provided according to the invention.

The guide means according to the invention may be associated with any type of implanted device, including joint-replacement components, nails, stems or other components. In each case, however, at least a portion of the guide means are preferably left exposed following initial fixation of the implant, enabling the surgeon to readily ascertain where the cutting tool needs to be inserted to sever the interface.

The invention is applicable to both cemented and non-cemented interfaces incorporating porous or bony ingrowth surfaces. In the case of the latter, the interface may be severed between the ingrowth region and surrounding bone, or between the ingrowth region and the body of the implant.

BRIEF DESCRIPTION OF THE DRAWINGS

FIG. 2A is a side-view drawing of an inventive prosthesis having means to guide an osteotome to separate the interface between the step of the implant and surrounding bone;

FIG. 2B is a drawing of the arrangement of FIG. 2A with the osteotome inserted and advancing partially down along the side of the stem of the prosthesis;

DETAILED DESCRIPTION OF THE INVENTION

Figure 1A:
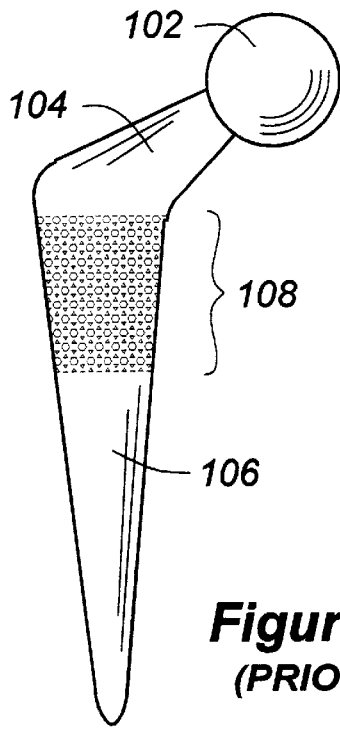
FIG. 1A is a side-view drawing of a prior-art proximal femoral endoprosthesis including bony ingrowth section.
Figure 1B:
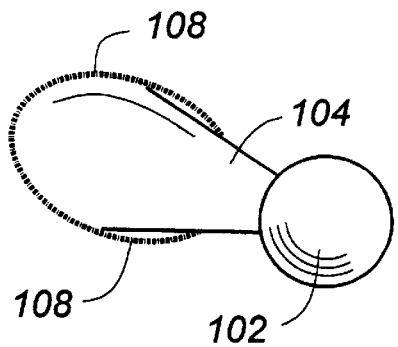
FIG. 1B is a top-view drawing of the prior-art element of FIG. 1A.

FIGS. 1A and 1B illustrate a typical, prior-art proximal femoral endoprosthesis including a section of bone-ingrowth material 108. Those knowledgeable in the field of orthopaedics will appreciate that the particular configuration of the ingrowth material varies between manufacturers. FIG. 1A illustrates the device from the side-view perspective, whereas FIG. 1B is a top-down view. In this particular case, the device includes a head portion 102 attached to a neck portion 104, and a stem portion 106.

As discussed elsewhere, although this description centers on the application of the invention to a femoral prosthesis including a bony or porous ingrowth section, the invention is equally applicable to other types of prosthesis, whether cementless or cemented. That is, the cutting guide means may be applied to other types of devices having different geometries, while, nevertheless, enabling a more controlled separation from surrounding bone.

FIG. 2A illustrates a proximal femoral endoprosthesis according to the invention. The device is similar to that shown in FIGS. 1A and 1B, but, along at least a portion of the stem there is provided guide means to direct a cutting tool along the implant/bone interface. In this particular embodiment, the guide means are in the form of tracks 206 which are used to guide an osteotome 208.

Figure 3A:
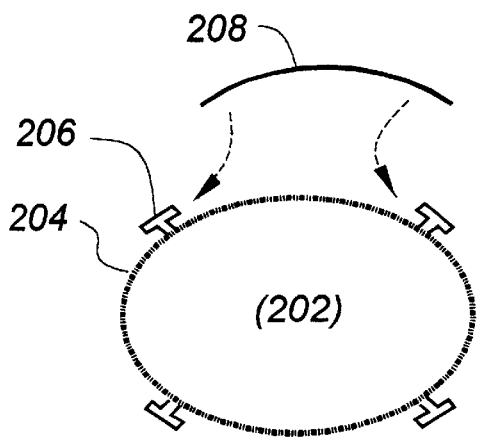
FIG. 3A is a cross-section of the implant of FIGS. 2A and 2B, showing how multiple guides may be provided for a more complete severance of the implant from surrounding bone.

FIG. 2B illustrates how the osteotome 208 has been partially received by the tracks 206, and having been advanced approximately halfway through the bony ingrowth section of the implant stem. FIG. 3A is a cross-section of the device of FIGS. 2A and 2B, as shown with the section indication. In the preferred embodiment, a plurality of guide means are provided around the entire stem of the implant, enabling a cutting tool to be inserted at different points, thereby providing a more complete separation from the surrounding bone.

Figure 3B:
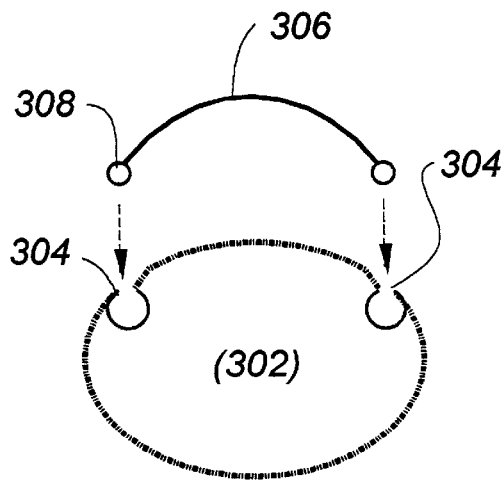
FIG. 3B is a cross-section of an alternative embodiment of the invention, wherein the guide means includes a plurality of channels formed in the surface of the implant.

In alternative embodiments of the invention, grooves, channels or slots may be formed into the surface of the implant stem to act as cutting-tool guide means. FIG. 3B is a cross section of one such alternative embodiment, wherein channels 304 are provided to receive a specially prepared cutting tool 306 having edges 308 to mate with the channels 304. Note that a standard cutting tool such as an osteotome may also be deployed according to this embodiment, in which case the channels 403 may be sized to receive the flat edges of the tool.

Should the osteotome or other cutting tool feature a curved or flexible blade, it may be directed into the channels by flexing the blade, after which it may be tapped down along the side of the implant to break it away from the host. Note that, in the preferred embodiment, at least a portion of the guide means remain at least partially exposed after fixation of the inventive implant, enabling the practitioner to easily determine where the cutting tool needs to "get started" to initiate the removal process.

Figure 4:
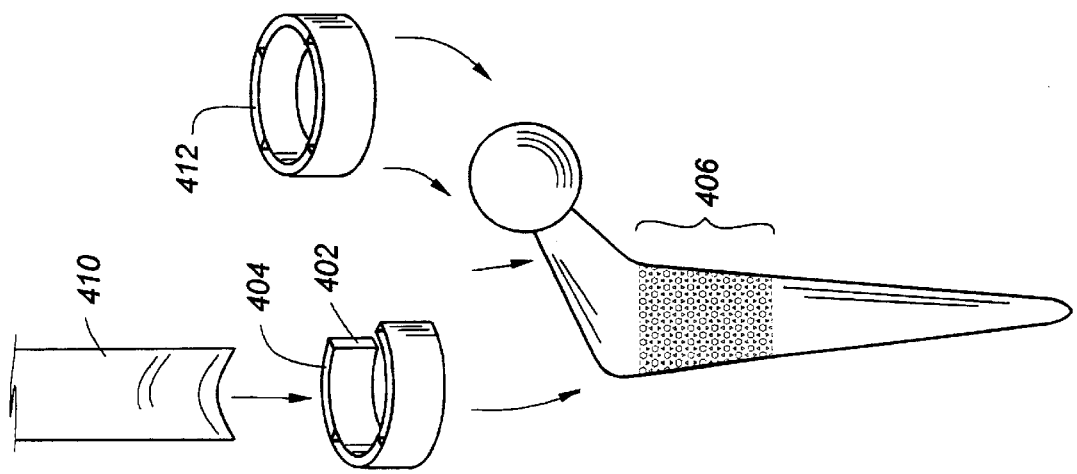
FIG. 4 illustrates an alternative embodiment of the invention, wherein guide means are provided on a separate component which is aligned with a prosthetic element.

Now making reference to FIG. 4, as an alternative to the placement of the cutting-tool guides on the prosthesis itself, a separate component may be provided, which includes the guide means. This separate component may then be aligned to the implant and used in a manner similar to the case in which the capture means are provided on the prosthesis itself. In the particular embodiment depicted in FIG. 4, a guide ring is placed over an exposed portion of the implant. In the particular case of a femoral prosthesis 406, a horseshoe-shaped element 402 featuring guides 404 may be employed or, if the ring fits over the head of the prosthesis, a more complete ring 412 may be used. In either case, the guide is placed onto an outwardly exposed portion of the stem of the prosthesis 406, enabling an osteotome or other cutting device 410 to be guided thereby to sever the implant from the surrounding host.

Figure 6:
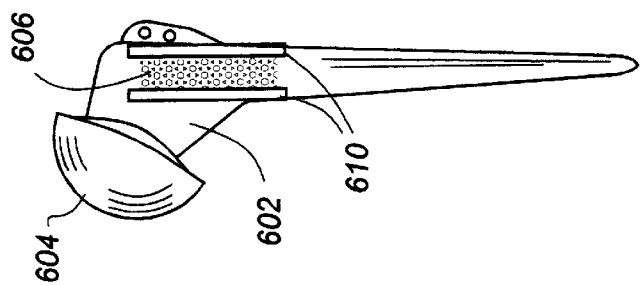
FIG. 6 shows a different alternative embodiment of the invention, wherein guide means are provided on a humeral prothesis.
Figure 5:
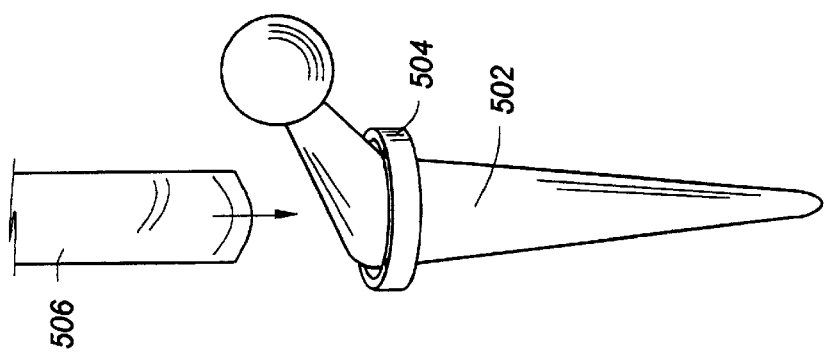
FIG. 5 is a drawing of a different alternative embodiment of the invention, wherein the guide means are physically coupled to as exposed portion of a prosthetic element, in this case the collar of a proximal femoral implant.

As yet a further alternative, guide means may be more permanently attached to a portion the prosthesis which remains accessible after fixation. For example, as shown in FIG. 5, the collar 504 of a femoral endoprosthesis 502 may serve the additional function of providing means to guide a cutting tool 506. As discussed above, the invention is applicable to any type of implanted device, including nails, stems, and other joint-replacement components. FIG. 6 shows how guides 610 may be applied to a humeral prosthesis 602 having a head portion 604.

Figure 7B:
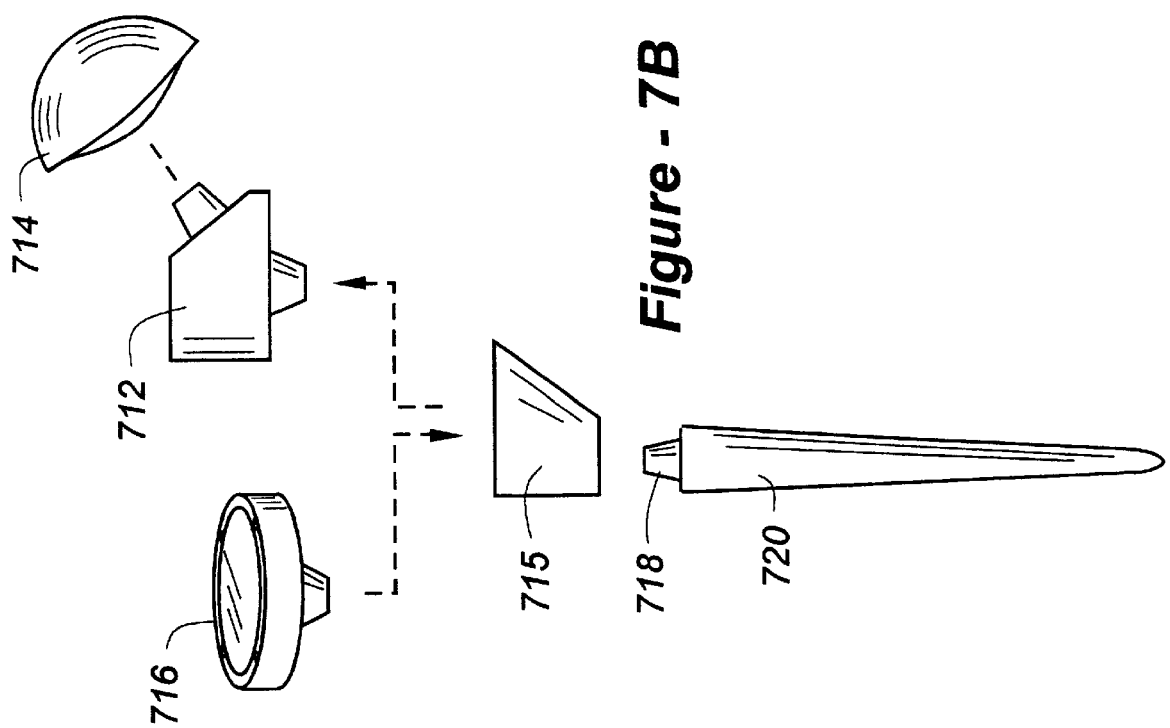
FIG. 7B depicts yet a further alternative embodiment of the invention, wherein guide means according to the invention replace one or more modular components associated with a humeral prothesis.
Figure 7A:
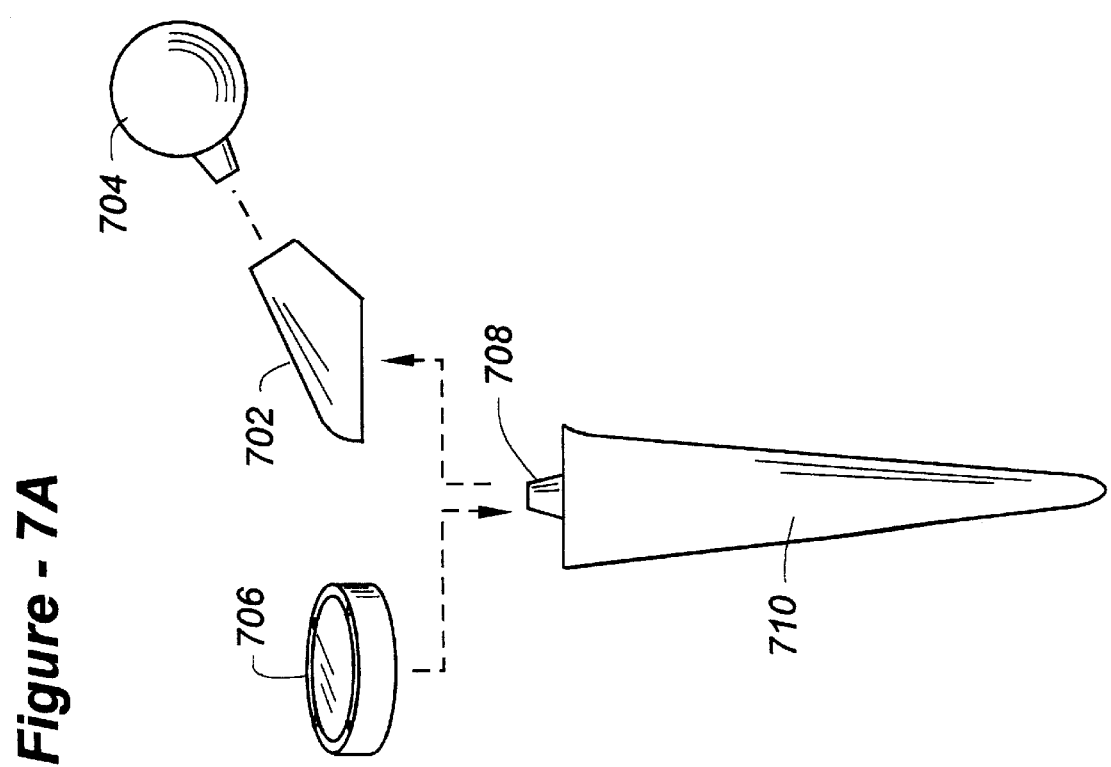
FIG. 7A depicts a further alternative embodiment of the invention, wherein guide means according to the invention replace one or more modular components associated with a proximal femoral prothesis.

Although the prosthesis 602 is shown with an ingrowth region 606, the invention is also applicable to cemented arrangements, as discussed elsewhere herein and shown in FIGS. 5 and FIGS. 7A–7B. The inventive guide means may also be used to replace modular components in hip, shoulder, or other implant systems. In FIG. 7A, a modular neck component 702 used to connect a stem 710 to a ball portion 704 with tapered-metal joints may be disassembled, and the neck component 702 replaced with a guide means 706. A modular hip system of this kind is depicted in U.S. Pat. No. 5,181,928. In FIG. 7B, guide means 716 replace modular components 712 and 714 in a shoulder system. One such system is disclosed in U.S. Pat. No. 5,902,340, which also uses an intermediate spacer 715 connecting to a stem 720 through tapered-metal joint 718. Those of skill will readily appreciate that the invention is applicable to modular systems other than those shown in FIGS. 7A and 7B.

Figure 8:
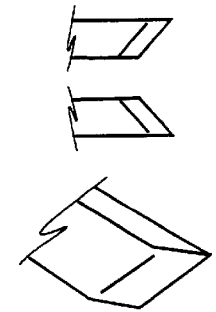
FIG. 8 illustrates specialized cutting tools associated with the invention which are less susceptible to binding up as the tool is advanced

Standard osteotomes are preferably used in conjunction with the invention, as discussed above. Alternatively, however, as shown in FIG. 8, specialized cutting tools may be provided to minimize binding. In particular, osteotomes with front-to-back and/or left/right bevels may be provided, as appropriate, to ensure that the device does not bind as it advances downwardly between the prosthesis and the surrounding host bone. The flexibility of the blade, as well as radius of curvature at the cutting edge, may also be varied, depending upon the given situation.

I claim:

1. Apparatus for use with a cutting tool to remove a prosthesis having an implanted portion with an outer surface defining an interface relative to surrounding bone, the apparatus comprising:
    guide means in alignment with at least a portion of the outer surface of the prosthesis to direct the cutting tool into the interface to facilitate a controlled separation of the prosthesis from the surrounding bone.

2. The apparatus of claim 1, wherein the guide means are provided on the prosthesis.

3. The apparatus of claim 1, wherein the guide means are provided separately from the prosthesis.

4. The apparatus of claim 1, wherein the interface is a cemented interface.

5. The apparatus of claim 1, wherein the interface is a cementless interface.

6. The apparatus of claim 5, wherein the cementless interface includes a section of bony ingrowth material.

7. The apparatus of claim 1, wherein the cutting tool is a osteotome having a blade.

8. The apparatus of claim 1, wherein the guide means are in the form of spaced-apart tracks formed on the outer surface of the prosthesis.

9. The apparatus of claim 1, wherein the guide means are in the form of spaced-apart channels, grooves or slots formed into the outer surface of the prosthesis.

10. The apparatus of claim 1, wherein the prosthesis is a proximal femoral prosthesis.

11. The apparatus of claim 1, wherein the prosthesis is a humeral prosthesis.

12. Apparatus for use with a cutting tool for removing a prosthesis, comprising:
    a prosthesis having an implanted portion with an outer surface defining an interface relative to surrounding bone; and guide means to receive the cutting tool, the guide means being aligned to the outer surface of the prosthesis, so that as the guided cutting tool is advanced therewithin, an associated portion of the interface is severed.

13. The apparatus of claim 12, wherein the guide means are provided on the prosthesis.

14. The apparatus of claim 12, wherein the guide means are provided separately from the prosthesis.

15. The apparatus of claim 12, wherein the interface is a cemented interface.

16. The apparatus of claim 11, wherein the interface is a cementless interface.

17. The apparatus of claim 16, wherein the cementless interface includes a section of bony ingrowth material.

18. The apparatus of claim 12, wherein the cutting tool is a osteotome having a blade.

19. The apparatus of claim 12, wherein the guide means includes one or more spaced-apart tracks on the outer surface of the prosthesis.

20. The apparatus of claim 12, wherein the guide means includes one or more spaced-apart channels, grooves, or slots formed in the outer surface of the prosthesis.

21. The apparatus of claim 12, wherein the prosthesis is a proximal femoral prosthesis.

22. The apparatus of claim 12, wherein the prosthesis is a humeral prosthesis.

* * * * *